US00PP32645P3

(12) United States Plant Patent
Kenworthy et al.

(10) Patent No.: US PP32,645 P3
(45) Date of Patent: Dec. 15, 2020

(54) ST. AUGUSTINEGRASS PLANT NAMED 'FSA1602'

(50) Latin Name: *Stenotaphrum secundatum* (Walt.) Kuntze
Varietal Denomination: FSA1602

(71) Applicant: Florida Foundation Seed Producers, Inc., Marianna, FL (US)

(72) Inventors: Kevin E. Kenworthy, Gainesville, FL (US); Kenneth H. Quesenberry, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 16/501,837

(22) Filed: Jun. 14, 2019

(65) Prior Publication Data

US 2019/0387655 P1 Dec. 19, 2019

Related U.S. Application Data

(60) Provisional application No. 62/685,156, filed on Jun. 14, 2018.

(51) Int. Cl.
*A01H 5/12* (2018.01)
*A01H 6/46* (2018.01)

(52) U.S. Cl.
USPC ..... Plt./392
CPC ..... *A01H 6/46* (2018.05)

(58) Field of Classification Search
USPC ..... Plt./384, 392
See application file for complete search history.

(56) References Cited

U.S. PATENT DOCUMENTS

PP7,852 P 4/1992 Busey
PP9,395 P 12/1995 Kirkland et al.
PP21,280 P3 9/2010 Nagata et al.

*Primary Examiner* — Susan McCormick Ewoldt
*Assistant Examiner* — Karen M Redden
(74) *Attorney, Agent, or Firm* — Dentons US LLP

(57) ABSTRACT

'FSA1602' is a new and distinct St. Augustine grass (*Stenotaphrum secundatum* (Walt.) Kuntze) variety distinguished at least by its distinctive olive blue-green color, large stolon size, and good tolerance to leaf diseases.

3 Drawing Sheets

ACKNOWLEDGEMENT OF FEDERAL RESEARCH SUPPORT

This invention was made with government support under 2015-51181-24291 awarded by the National Institute of Food and Agriculture, United States Department of Agriculture (U.S.D.A.). The government has certain rights in the invention.

Latin name of the genus and species of the plant claimed: *Stenotaphrum secundatum* (Walt.) Kuntze.

Variety denomination: 'FSA1602'.

BACKGROUND OF THE INVENTION

The present invention relates to a new and distinct asexually reproduced variety of St. Augustine grass (*Stenotaphrum secundatum* (Walt.) Kuntze) designated 'FSA1602'. 'FSA1602' originated from a cross of 'NUF-216' (unpatented) and 'Floraverde' (unpatented and also designated as 'FL-1997-6'). 'FSA1602' was first asexually reproduced in Gainesville, Fla. in 2010 by obtaining vegetative cuttings of stolons, further cutting those stolon cuttings into segments exhibiting at least one vegetative bud, and rooting those segments in potting media. Asexually reproduced plants of 'FSA1602' have remained stable and true to type through at least six cycles of repeated vegetative propagation. No seedling establishment from 'FSA1602' has been noticed in greenhouse or field trials. 'FSA1602' has a polyploid chromosome number similar to that of 'Floratam' (unpatented) and 'Floralawn' (unpatented).

SUMMARY OF THE INVENTION

'FSA1602' is a perennial St. Augustine grass, and was identified in 2010 as distinctly different from other St. Augustine grass varieties based at least on its distinctive olive blue-green color, large stolon size, and good tolerance to leaf diseases. 'FSA1602' spreads by stolons and has been propagated by tillers and sod. 'FSA1602' can be unambiguously distinguished from the other turf grass varieties in the source collection from Belle Glade, Fla. and aneu-polyploid St. Augustine grass varieties at least based on its distinct olive blue-green leaf color. For example, the distinct olive blue-green color of 'FSA1602' distinguished it from 28 other experimental lines as well as the control cultivars 'NUF-76' (U.S. Plant Pat. No. 21,280), 'Floratam' (unpatented), 'Floraverde' (unpatented and also designated as 'FL-1997-6'), and 'SS-100' (U.S. Plant Pat. No. 09,395) that were grown near Gainesville, Fla. and Citra, Fla. Further, 'FSA1602' can be unambiguously distinguished from diploid St. Augustine grass varieties at least based on its stolon size and courser leaf texture. Additionally, 'FSA1602' is distinguishable from both of its parents, 'NUF-216' and 'Floraverde', by its stolon length, leaf length, internode length, and stolon diameter. Specifically, 'FSA1602' exhibits shorter stolon length, leaf length, and internode length, with a larger stolon diameter than 'NUF-216' and 'Floraverde'.

'FSA1602' may be used as a turfgrass that is suitable for home lawns and commercial turf applications. While 'FSA1602' exhibited good turfgrass performance and temperature adaptation when tested as far north as Raleigh, N.C. (U.S.D.A. hardiness zone 7b), it is best adapted to the southern and gulf coast regions of the U.S.A., including South Carolina, Georgia, Florida, Alabama, Mississippi, Louisiana, and Texas. Further, 'FSA1602' is well adapted to those regions where St. Augustine grasses are currently grown, including regions of New Mexico, Arizona, and California, and other subtropical and tropical areas worldwide.

BRIEF DESCRIPTION OF THE DRAWINGS

This new St. Augustine grass plant is illustrated by the accompanying photographs of plants grown in a Gainesville, Fla. greenhouse. The photographs show the plant's typical form, foliage, and inflorescence, and the colors shown are as true as can be reasonably obtained by conventional photographic procedures.

DETAILED BOTANICAL DESCRIPTION

Figure 1:
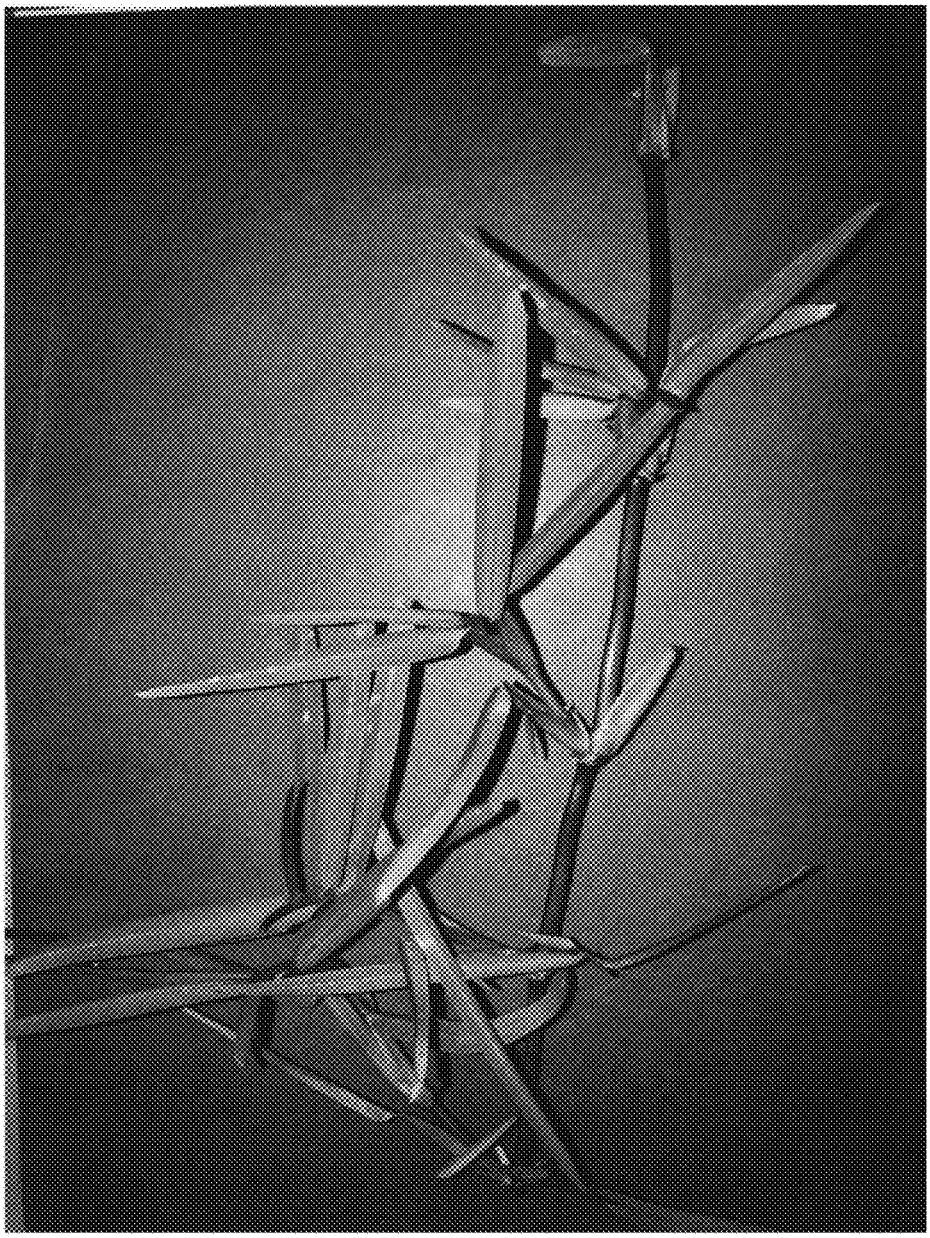
FIG. 1—Shows a stolon of the claimed plant.
Figure 2:
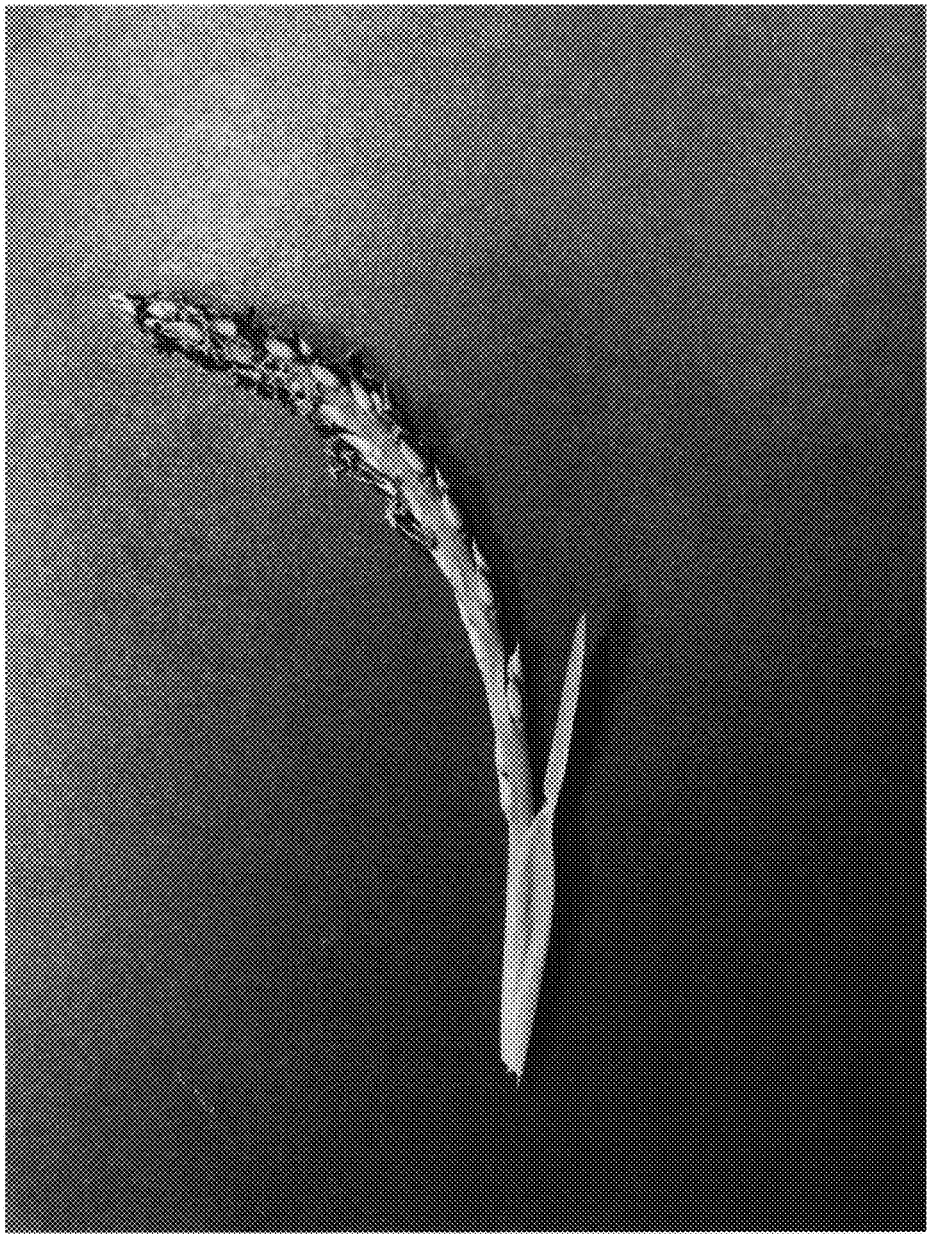
FIG. 2—Shows an inflorescence, including anthers and stigmas, of the claimed plant.
Figure 3:
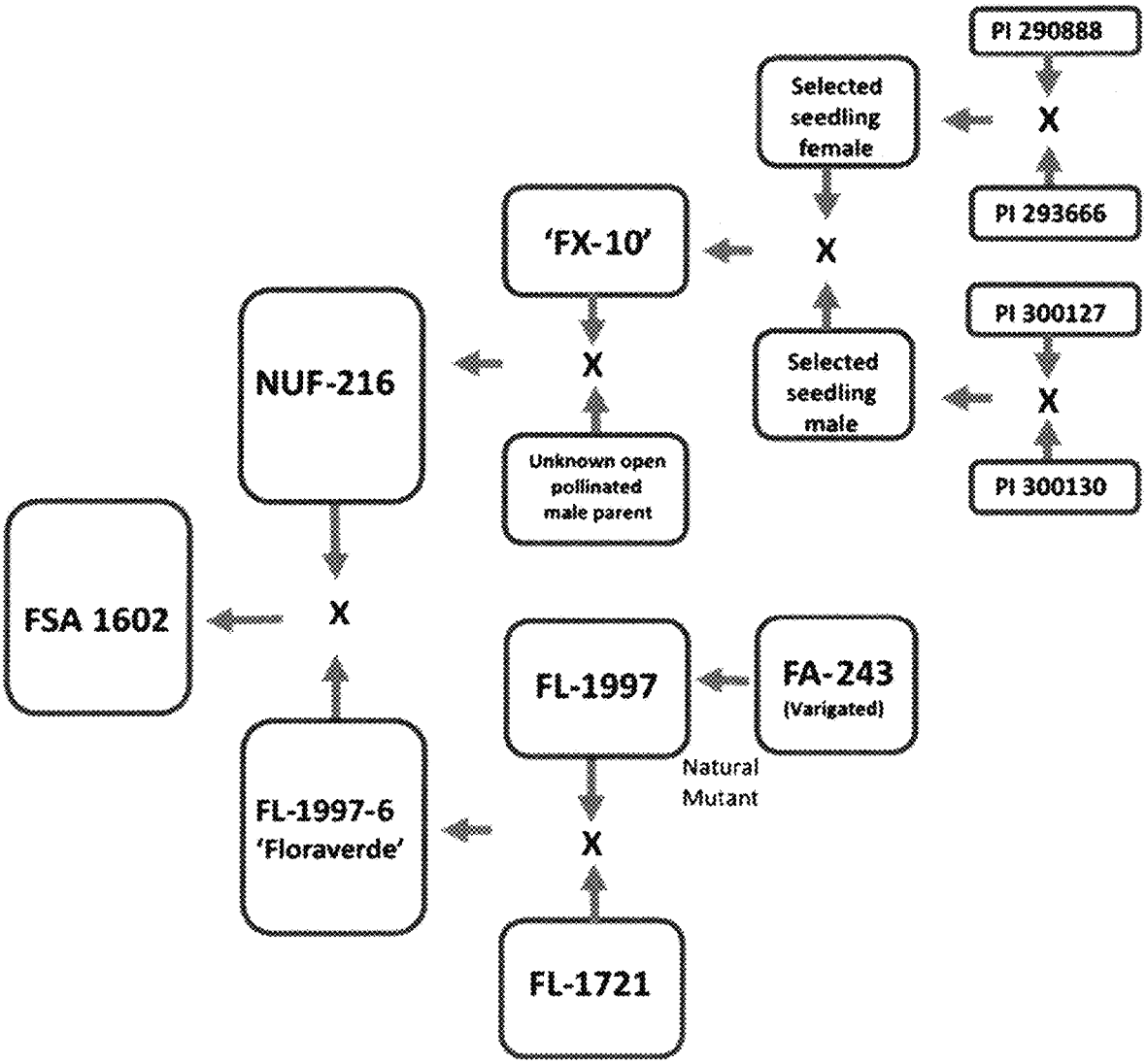
FIG. 3—Shows the pedigree of the claimed plant in which it was selected as a seedling from the cross of 'NUF-216' (unpatented) and 'Floraverde'. 'NUF-216' is a seedling from 'FX-10' (U.S. Plant Pat. No. 7,852) by an unknown open-pollinated male, and 'Floraverde' resulted from the cross of 'FL-1997' (unpatented) x 'FL-1721' (unpatented).

The following detailed description sets forth distinctive characteristics of 'FSA1602', as characterized in greenhouse and field conditions in Florida. The data that define these characteristics were collected from asexual reproductions approximately ten weeks after initial pot establishment. 'FSA1602' has not been observed under all possible environmental conditions, and the measurements given may vary when grown in different environments. Certain characteristics may also vary with plant age. The color descriptions provided herein are based on The Royal Horticultural Society (R.H.S.) Colour Chart by The Royal Horticultural Society, London, Sixth Revised Edition. If any R.H.S. color designations below differ from the accompanying photographs, the R.H.S. color designations are accurate.

MORPHOLOGICAL COMPARISON OF 'FSA1602' TO COMMERCIAL VARIETIES

The morphological characteristics of 'FSA1602' and commercial St. Augustine grass varieties 'SS-100' and 'Floratam' were compared head-to-head in 2015 using potted plants that were approximately 6 months in age. The plants were grown and compared in a greenhouse located near Gainesville, Fla., with a nighttime low of 60° F. and daytime high of 90° F. The plants were grown under natural day length without supplemental lighting, and fertilized using a soluble fertilizer of 20-20-20 in four equal soluble applications per month, which equated to approximately one pound of nitrogen (N) per month. Leaf length (cm) and width (cm) were measured on the second fully expanded leaf below the growing meristem of a stolon. The number of lateral shoots per pot and the length of lateral shoots (cm) from the crown of the pot were measured after 3 months of regrowth. The length of the third internode below the growing meristem (cm) and the stolon diameter between the second and third internodes (mm) were also measured. Table 1 provides the measurements of these seven characteristics.

The leaves of 'FSA1602' exhibited a medium-fine texture, and these leaves were wider than those of 'SS-100' but similar to those of 'Floratam'. The leaves of 'FSA1602' also exhibited a blade length that was shorter than that of 'Floratam' leaves but was similar to that of 'SS-100' leaves. The average observed length of 'FSA1602' internodes was shorter than that of either 'Floratam' or 'SS-100' internodes, which indicates 'FSA1602' exhibits a higher density of vegetative shoots in sod plots as well as a higher turfgrass density ratings than those two varieties. The average observed diameter of 'FSA1602' stolons was larger than that of either 'Floratam' or 'SS-100' stolons. With respect to lateral shoot growth, all three varieties produced a similar number after three months of regrowth, and there was no noticeable difference between the three varieties in the average observed length of these shoots. Most notably, 'FSA1602' plants displayed a distinct dark olive blue-green color that was unambiguously distinguishable from the color of 'Floratam' and 'SS-100' plants.

MORPHOLOGICAL COMPARISON OF 'FSA1602' TO PARENTAL VARIETIES 'NUF-216' AND 'FLORAVERDE'

The morphological characteristics of 'FSA1602' and parental varieties 'NUF-216' and 'Floraverde' were compared head-to-head in February 2020. The plants were grown and compared in a greenhouse located near Gainesville, Fla. Stolon length, leaf length and width, internode length, and stolon diameter were measured. Leaf length (cm) and width (cm) were measured on the mature leaf arising from the stolon node nearest the edge of the pot. The internode length (cm) and stolon diameter (cm) were measured on the fourth internode from the tip of the stolon. Table 3 provides the measurements of these five characteristics.

The following are additional unique and distinguishing characteristics exhibited by 'FSA1602' when grown under the above greenhouse conditions:

Plant:

- *Growth habit*.—A perennial plant that spreads by stolons and produces a dense and somewhat coarse textured turfgrass.
- *Plant height* (*from soil*).—Mean of 12.5 cm.
- *Root characteristics*.—Typically develops fibrous roots from nodes that are in contact with the soil, ultimately forming a sod of fibrous rooted plants.
- *Rhizomes*.—Not observed.
- *Flowering*.—Indeterminate.
- *Fruit* (*caryopses*).—Not observed.
- *Leaf blade color adaxial leaf surface*.—126B moderate bluish green.
- *Leaf blade color abaxial leaf surface*.—126B moderate bluish green.
- *Stolon color* (*area under leaf sheath*).—200C moderate brown.

Leaves:

- *Leaf blade attachment*.—The leaf lamina is constricted at the base, at the point of attachment to the leaf sheath.
- *Leaf blade shape*.—Linear.
- *Leaf blade apex shape*.—Acute.

*Leaf aspect in initial leaves*.—Tend to be upright, varying from near completely upright (90 degrees) to intermediate (45 degrees) in relation to the soil surface.

*Leaf aspect in established sod*.—Varies from near parallel to the soil surface to intermediate.

*Lower surface leaf blade texture*.—Smooth.

*Upper surface leaf blade texture*.—Rough.

*Leaf blade margins*.—Rough.

*Leaf blade venation*.—Parallel.

*Leaf collar*.—Continuous.

*Leaf ligule*.—Thin, membranous, and approximately 1 to 2 mm in length.

*Auricle*.—Not present, but some hairs are present along the leaf margins near the collar region.

*Culm length*.—Mean of 6.5 cm when measured from the node of the flag leaf to the position of the first floret on the spike-like raceme.

Florets:

*Florets per spike*.—Mean of 30.

*Floret size*.—Approximately 4.0 mm in length with an acute apex.

*Stigma shape*.—Feather shaped with a central axis and numerous lateral branches, typical of St. Augustine grass.

*Ovary size*.—Fertilized ovules at 10 to 12 days post pollination and are approximately 2 to 3 mm in length.

*Ovary color*.—RHS 157D light greenish white.

Inflorescence: Produces both terminal and axillary spikes, with spikelets embedded in the flattened corky rachis. The spiklets generally occur in pairs or, sometimes, triads.

*Average raceme length*.—7.0 cm.

*Culm stalk color*.—144C strong yellow green.

*Rachis color*.—146B moderate yellow green.

*Stigma color*.—N81B strong purple.

*Anther color*.—17A strong orange yellow.

TURF QUALITY, COLOR, AND DENSITY COMPARISON OF 'FSA1602' TO COMMERCIAL VARIETIES

'FSA1602' has been evaluated in field plot trials conducted near Citra, Fla. (Latitude: 29.41, Longitude: −82.17) and Jay, Fla. (Latitude: 30.78, Longitude: −87.14). In these trials, the turfgrass quality, color, and density of the entries were evaluated using the industry recognized rating systems established by the United States Golf Association (U.S.G.A.). Turfgrass quality was rated on a "1" to "9" scale in which "9" indicates "best," "6" indicates "minimally accepted," and "1" indicates "poorest"; turfgrass color was rated on a "1" to "9" scale in which "9" indicates the darkest green; and turfgrass density was rated on a "1" to "9" scale in which "9" indicates "best," "6" indicates "minimally accepted," and "1" indicates "poorest." Entries for 'FSA1602', 'Floratam', and 'SS-100' were established in July of 2011 from rooted plugs such that there were three replicates of each variety at both locations, and these entries were maintained as standard turfgrass plots that were mowed at 7.5 cm height. These entries were regularly observed and rated through the end of 2016.

Data obtained from these trials is provided in Table 2. For the trial near Citra, Fla., the average turf grass quality of the tested varieties in the winter and summer of 2016 are provided. The winter rating reflects the average of observations made in January and February and the summer rating reflects the average of observations made in April, September, and October. Large patch (LP) disease (*Rhizoctonia solani*) was also prevalent at the Citra, Fla. location, and the average turf grass quality of the tested varieties during periods of large patch disease prevalence is provided. This rating reflects the average of observations made in February and December of 2013, and December of 2015. Also, turf quality was measured in May of 2014 after a period of drought at the Citra, Fla. location in which irrigation was also withheld. For the trial near Jay, Fla., turf quality, color, and density data is provided as an average of the observations made in April, May, June, July, August, September, and October of 2016, and as the average of 24 observations made over the full duration of the 5-year trial.

At the Citra, Fla. location, 'FSA1602' displayed superior summer turfgrass quality in comparison to both 'Floratam' and 'SS-100'; whereas, the winter turfgrass quality displayed by 'FSA1602' was more similar to that of 'Floratam' but still superior to that of 'SS-100'. In the presence of large patch disease, the quality of 'FSA1602' was superior to that of 'SS-100' but similar to that of 'Floratam'. In response to drought, 'FSA1602' maintained its quality better than 'SS-100' but similar to 'Floratam'. At the trial near Jay, Fla., 'FSA1602' achieved superior turfgrass quality and density ratings in comparison to both 'Floratam' and 'SS-100' when the observations made over 2016 were averaged; whereas, the average turfgrass color achieved by 'FSA1602' was similar to that of 'Floratam' but superior to that of 'SS-100'. Notably, 'FSA1602' also achieved superior turfgrass color, quality, and density ratings in comparison to both 'Floratam' and 'SS-100' when the observations made over the course of the five-year trial were averaged. The averages of the 24 observations made over the course of the 5-year trial also best reflects the long-term performance of these varieties, and superior long-term performance is strongly indicative of the overall merit of a turfgrass variety. Also in both field trials, the color of 'FSA1602' most closely resembled the color RHS 126B (moderate bluish green); whereas both 'Floratam' and 'SS-100' most closely resembled RHS N138B (moderate yellowish green).

TABLE 1

Morphological comparison of 'FSA1602' and commercial St. Augustine grass varieties.

| Variety | Leaf length | Leaf width | No. of lateral shoots | Lateral shoot length | Internode length | Stolon diameter |
|---|---|---|---|---|---|---|
| 'FSA1602' | 6.00b | 0.92a | 11.67a | 18.50a | 4.50b | 3.82a |
| 'Floratam' | 8.50a | 0.98a | 10.33a | 22.72a | 6.22a | 3.46b |
| 'SS-100' | 6.50b | 0.78b | 12.67a | 18.83a | 6.42a | 2.80c |
| LSD (p = 0.05) | 0.6 | 0.06 | 2.50 | 6.95 | 1.23 | 0.15 |

Means in a column followed by the same letter are not significantly different at p = 0.05

TABLE 2

Turf comparison of 'FSA1602' and commercial St. Augustine grass varieties at two locations.

| | Citra, FL Quality | | | |
|---|---|---|---|---|
| Variety | Winter | Summer | LP | Drought |
| 'FSA1602' | 5.8 | 7.0 | 7.2 | 7.0 |
| 'Floratam' | 4.9 | 5.7 | 6.8 | 6.3 |
| 'SS-100' | 4.2 | 4.5 | 4.3 | 4.7 |
| LSD (p = 0.05) | 1.3 | 1.3 | 0.7 | 1.2 |

TABLE 2-continued

Turf comparison of 'FSA1602' and commercial St. Augustine grass varieties at two locations.

| | Jay, FL | | | | | |
|---|---|---|---|---|---|---|
| Variety | Quality 2016 | Color 2016 | Density 2016 | Quality 5-year | Color 5-year | Density 5-year |
| 'FSA1602' | 7.4 | 7 | 7.6 | 7.1 | 7.0 | 7.2 |
| 'Floratam' | 6.3 | 6.2 | 6.4 | 5.5 | 6.0 | 5.7 |
| 'SS-100' | 6.1 | 5.5 | 6.3 | 5.8 | 5.7 | 6.1 |
| LSD(p = 0.05) | 0.6 | 0.8 | 0.5 | 0.8 | 0.3 | 0.6 |

TABLE 3

Morphological comparison of 'FSA1602', 'NUF-216', and 'Floraverde'.

| Variety | Stolon Length | Leaf Length[1] | Leaf Width[1] | Internode Length[2] | Stolon Diameter[2] |
|---|---|---|---|---|---|
| 'FSA 1602' | 18.1b | 5.52b | 0.75a | 3.52b | 5.07b |
| NUF-216 | 48.3a | 7.05a | 0.88a | 7.98a | 4.58a |
| Floraverde | 54.6a | 7.37a | 0.68a | 6.15a | 3.13a |
| LSD (p = 0.05) | 14.9 | 1.31 | 0.13 | 1.21 | 0.27 |

Means in a column followed by the same letter are not significantly different at p = 0.05
[1]Measurement of the mature leaf arising from the stolon node nearest the edge of the pot
[2]Measurements taken on the fourth internode from the tip of the stolon

What is claimed is:

1. A new and distinct variety of St. Augustine grass plant named 'FSA1602', as illustrated and described herein.

* * * * *